United States Patent [19]
Fujii et al.

[11] Patent Number: 5,965,071
[45] Date of Patent: Oct. 12, 1999

[54] PROCESS FOR PREPARING GRANULAR UREA

[75] Inventors: Hidetsugu Fujii; Haruyuki Morikawa, both of Chiba, Japan

[73] Assignee: Toyo Engineering Corporation, Toyko, Japan

[21] Appl. No.: 08/913,871

[22] PCT Filed: Jan. 21, 1997

[86] PCT No.: PCT/JP97/00108

§ 371 Date: Sep. 5, 1997

§ 102(e) Date: Sep. 5, 1997

[87] PCT Pub. No.: WO97/28100

PCT Pub. Date: Aug. 7, 1997

[30] Foreign Application Priority Data

Feb. 1, 1996 [JP] Japan ........................... 8-16541

[51] Int. Cl.⁶ ........................................... B29B 9/10
[52] U.S. Cl. .................................. 264/14; 264/5
[58] Field of Search ........................ 264/7, 14, 5

[56] References Cited

U.S. PATENT DOCUMENTS

| | | | |
|---|---|---|---|
| 3,059,280 | 10/1962 | Laehder | 264/14 |
| 3,067,177 | 12/1962 | Greco et al. | |
| 3,112,343 | 11/1963 | Allgeuer et al. | |
| 3,130,225 | 4/1964 | Friend | 264/14 |
| 3,686,373 | 8/1972 | Griesheimer et al. | 264/14 |
| 4,219,589 | 8/1980 | Niks et al. | 427/213 |
| 4,390,483 | 6/1983 | Willems et al. | 264/14 |

*Primary Examiner*—Mary Lynn Theisen
*Attorney, Agent, or Firm*—Flynn, Thiel, Boutell & Tanis, P.C.

[57] ABSTRACT

The present invention provides a process for preparing granular urea, which solves the problem of removing moisture in a prilling tower method and the problem of concentrating diluted formaldehyde in granulation by a fluidized, spouted bed method when urea is granulated in the presence of formaldehyde. That is, the present invention provides a process for preparing granular urea from liquid drops or sprayed drops of a urea solution, wherein the urea solution is divided into two portions of a urea solution A and a urea solution B, and a urea solution prepared by mixing an aqueous formaldehyde solution with the urea solution A, concentrating the above mixed solution and then mixing it with the urea solution B is used.

11 Claims, 1 Drawing Sheet

PROCESS FOR PREPARING GRANULAR UREA

FIELD OF THE INVENTION

The present invention relates to a process for preparing granular urea from liquid drops or sprayed drops of a urea solution. In the present invention, urea liquid is a general term for molten urea and an aqueous urea solution.

DESCRIPTION OF THE RELATED ART

Various processes for preparing granular urea are known. In general, a prilling tower method and a fluidized, spouted bed method are employed.

In the prilling tower method, an aqueous urea solution containing moisture of 0.1 to 0.3% by weight is caused to fall from the top of a prilling tower in the form of liquid droplets, and falling liquid drops are cooled and solidified by contacting them with an ascending air current coming from the bottom of the prilling tower, whereby urea particles called prill are produced.

Urea grains obtained by this method are relatively small (0.5 to 2.5 mm) and have a low mechanical strength.

The fluidized, spouted bed method is used to produce a grain which is larger than the grain produced by the prilling tower method and has a high mechanical strength and is specifically disclosed in U.S. Pat. No. 4,219,589 and JP-B-4-63729.

For example, a method is disclosed in JP-B-463729, in which a urea solution is fed in the form of fine liquid drops into a fluidized bed in which a spouted bed comprising urea seed grains is scattered, to adhere the urea solution on the urea seed particles, followed by drying and solidifying, whereby large-sized urea grains are produced.

As disclosed in U.S. Pat. No. 3,067,177, U.S. Pat. No. 3,112,343 and JP-B-50-34536, it is well known that in these processes for preparing granular urea by the fluidized, spouted bed method, an additive is added to a urea solution for the purposes of improving the mechanical strength and coagulation resistance of a large-sized urea grain product and enhance the granulating efficiency, that is, losing a part of the urea solution in the form of very fine dusts without it being used for forming the grains in granulating. This additive is an aqueous formaldehyde solution or a urea/formaldehyde reaction product (it is commercially available under a trade name of, for example, Formurea 80).

In the process for preparing prill urea by the prilling tower method, it is substantially impossible to remove moisture. The mechanical strength and coagulation resistance of the resulting urea grains can be improved by adding 0.3 to 0.6% by weight of formaldehyde. However, the use of an aqueous formaldehyde solution as a formaldehyde source results in the addition of a lot of water to the urea because the content of formaldehyde in the aqueous formaldehyde solution is usually 30 to 37% by weight and a large quantity of water is contained therein. This increases the moisture contained in the resulting urea grains and in turn deteriorates the quality of the urea grains. Accordingly, an aqueous formaldehyde solution can not be used for the prilling tower method in which the moisture in the process steps can not be removed.

On the other hand, a process for preparing large-sized urea grains by the fluidized, spouted bed method has the capability of evaporating the moisture to some extent in the granulating facility thereof. However, in the case where moisture exceeding the evaporation capability of the granulating facility is present, for example, in the case where a more diluted aqueous formaldehyde solution than that expected in designing can not help from being used, the water content of the urea and formaldehyde mixture has to be reduced down to a given level or lower before introducing it into the granulating facility.

As described above, an aqueous formaldehyde solution usually contains 30 to 37% by weight of formaldehyde and therefore contains a lot of water. The use of this aqueous formaldehyde solution concentrated simply to 37% by weight or more results in deteriorating the stability of the aqueous formaldehyde solution and depositing a polymer of formaldehyde, which in turn makes it difficult to feed formaldehyde in a prescribed amount.

Meanwhile, in granulating processes having no drying ability in a granulating mechanism, such as a pan type granulating method and a drum type granulating method, water has to be prevented from being mixed in. In these granulating processes, an aqueous formaldehyde solution can not be used as is the case with the prilling tower method.

SUMMARY OF THE INVENTION

An object of the present invention is to provide means for solving the problem of removing moisture in the prilling tower method and the problem of concentrating a diluted aqueous formaldehyde solution while granulating by the fluidized, spouted bed method, when urea is granulated in the presence of formaldehyde.

That is, the present invention relates to a process for preparing granular urea from a liquid drops or sprayed drops of a urea solution, wherein the urea solution is divided into two portions, a urea solution A and another urea solution B, and a urea solution prepared by mixing an aqueous formaldehyde solution with the urea solution A, concentrating the above mixed solution and then mixing it with the urea solution B is used; the process for preparing granular urea as described above, wherein the amount of the above urea solution A is controlled to 0.5 or more, based on the amount of formaldehyde added to the urea solution, in terms of molar ratio of urea/formaldehyde; and the process for preparing granular urea as described above, wherein the pH is adjusted to 6.5 or more when the above urea solution A is mixed with the aqueous formaldehyde solution and the mixed solution is concentrated.

In other words, the invention provides a process for preparing granular urea from liquid drops or sprayed drops of a urea solution, which comprises the steps of dividing the urea solution into two portions A and B, mixing the portion A with an aqueous formaldehyde solution, concentrating the mixture and mixing the concentrated mixture with the portion B and then granulating the mixture of portions A and B.

It is preferable that the portion A is mixed with the aqueous formaldehyde solution at a mole ratio of urea of the portion A to formaldehyde in the range of 0.5 or larger.

It is preferable that the mixing of the portion A with the aqueous formaldehyde solution and the concentration are conducted at a pH value of 6.5 or larger.

DETAILED DESCRIPTION OF THE INVENTION

Figure 1:
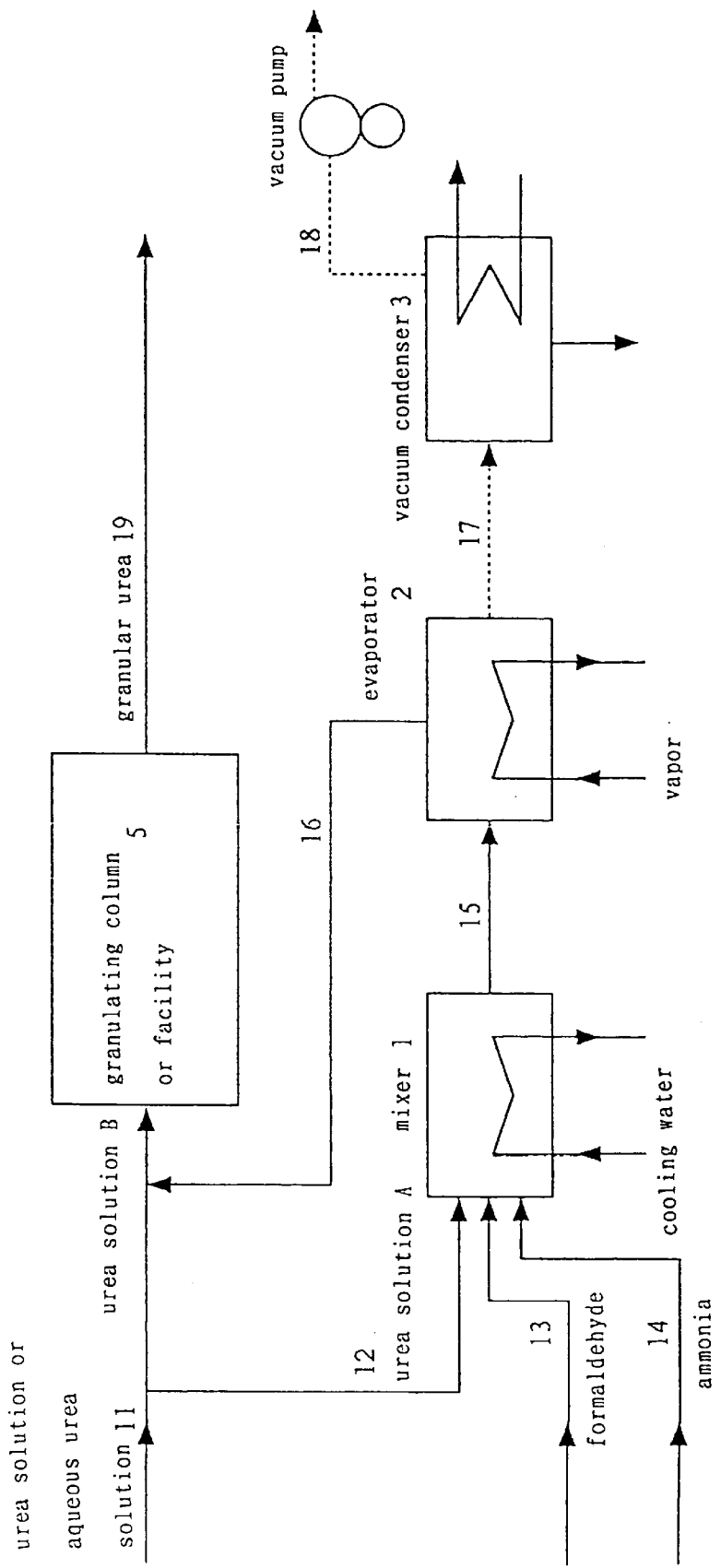
FIG. 1 is a schematic diagram showing the process for preparing granular urea according to the present invention.
Explanation of the Codes
1 Mixer
2 Evaporator
3 Vacuum condenser 4 Vacuum pump
5 Granulating column or facility

The present invention shall be explained below in detail.

FIG. 1 is a schematic diagram showing the process for preparing granular urea according to the present invention including a granulating facility (hereinafter called a granulating facility 5) based on the prilling tower method or the fluidized, spouted bed method. The facility according to the present invention comprises a mixer 1 in which the aqueous formaldehyde solution can be mixed with the urea solution and the mixed solution can be heated, an evaporator 2 for evaporating water contained in the mixed solution coming out of the mixer 1, and a vacuum condenser 3 for condensing evaporated water.

The urea solution is divided into the urea solution A and the urea solution B before the granulating facility 5, and as shall be described later, the urea solution B is mixed with the urea solution A which has been introduced into the granulating facility through a line 11.

The urea solution A is charged into the mixer 1 through a line 12. Introduced into the mixer 1 are the aqueous formaldehyde solution through a line 13 and ammonia through a line 14, respectively. In the mixer 1, the urea solution is homogeneously mixed with formaldehyde, and urea is reacted with formaldehyde if necessary. Conditions for this reaction shall be described later. The resulting mixture of the urea solution A and the aqueous formaldehyde solution is returned again to the line 11 through a line 16 after being concentrated in the evaporator 2, mixed with the urea solution B and then sent to the granulating facility 5.

The amount of the urea solution A is determined in such a manner that the addition amount of formaldehyde is determined so that the amount of formaldehyde is 0.3 to 0.6% by weight based on the amount of urea fed to the granulating facility 5 and the ratio of urea contained in the mixer 1 to the above formaldehyde amount is 0.5 or more in terms of the molar ratio of urea/formaldehyde. That is, the weight ratio A/T of the amount of the urea solution A to the total urea amount T is 2af, wherein f is the weight ratio of the formaldehyde amount/the total amount of urea, and a is the molar ratio of the amount of the urea solution A/the amount of formaldehyde.

A molar ratio of less than 0.5 is liable to increase the molar ratio of formaldehyde to urea and form a polymer of urea and formaldehyde.

If the molar ratio is increased more than needed, for example, 5.0 or more, the amount of urea heated is increased more than needed when the mixture of urea and formaldehyde is heated and used as a reaction product of urea and formaldehyde, which results in increasing the formation of biuret, which is a by-product. In usual cases, the amount of the urea solution A is a very small value based on the total amount of urea.

The urea solution A and formaldehyde contribute sufficiently to an improvement in the mechanical strength and coagulation resistance of the large-sized urea grain product only by mixing and concentrating (the divided urea solutions have a chance to be heated and reacted at the time when they are put together again and sent to the granulating facility 5). However, as shall be described later, they are more preferably reacted in advance to such an extent that polymerization is not caused (hereinafter both the mixed solution of the urea solution A and formaldehyde, and the reaction solution of them are called mixed solutions).

In the reaction of urea with formaldehyde, the lower the pH of the mixed solution is and the higher the temperatures are, the more easily the polymer of urea and formaldehyde is formed. In order to prevent this polymer from being formed, the pH is preferably maintained at 6.5 or higher by feeding ammonia gas or aqueous ammonia. A pH of less than 6.5 is liable to form the polymer of urea and formaldehyde and increase the polymerization rate, even if the reaction temperature is maintained low. Accordingly, the polymer is formed before concentration, and substantial concentration becomes impossible.

However, a pH of 9.5 or higher retards the reaction rate and increases the amount of formaldehyde which has not reacted with the urea. Further, formaldehyde is evaporated to a gas by heating in a concentration step, and more formaldehyde is consumed for providing the formaldehyde amount based on a prescribed urea amount. Further caused are the problems that the consumed amount of ammonia is increased more than needed and the ammonia odor damages the workability, and therefor the pH has to be restricted to less than 9.5.

The reaction of urea, formaldehyde and ammonia is an exothermic reaction, and the temperature of the mixed solution is elevated due to the reaction heat. Accordingly, the heat has to be removed by cooling water. This removal of heat for maintaining a suitable temperature is important for preventing the polymer from being formed. That is, the reaction temperature is maintained preferably at 40 to 100° C. at a condition of a pH of 6.5 or higher. A temperature of lower than 40° C. retards the reaction rate, and a temperature exceeding 100° C. forms the polymer in some cases before the concentration step.

The mixed solution obtained in the mixer 1 is introduced into the evaporator 2 through a line 15 for concentration. The evaporator 2 is fed with heat needed for evaporation by steam to evaporate and remove a part of the water from the mixed solution. The operating pressure is preferably controlled to a vacuum degree of such an extent that the temperature of the solution is not elevated by heating. The vacuum is formed by a vacuum pump 4 disposed downstream of the vacuum condenser 3. Steam evaporated from the evaporator 2 is sent to the vacuum condenser 3 through a line 17 to be cooled into condensed water and discharged to the outside of the system.

On the other hand, the mixed solution concentrated to a prescribed concentration is returned again to the urea solution line 11 through the line 16 and mixed with the urea solution B. Then, it is sent to the granulating facility to prepare granular urea.

In the present invention, a portion of the urea solution is withdrawn as the urea solution A before the granulating facility and mixed with the aqueous formaldehyde solution. Then, the mixed solution is concentrated and used again for preparing granular urea together with the remaining urea solution B. Accordingly, granular urea can be prepared without increasing the moisture contained in the product. The urea solution A withdrawn from the urea solution is maintained at 0.5 or more in terms of the molar ratio of urea/formaldehyde, and therefore the polymerization caused in heating and concentrating is controlled. Since the urea solution A is reacted with formaldehyde under the condition of a pH of 6.5 or higher, polymerization is suppressed.

In the present invention, a portion of the urea solution is withdrawn as urea solution A before the granulating facility. Formaldehyde is added to it and the resulting mixture is concentrated and mixed again with the remaining urea solution B to prepare granular urea. Accordingly, diluted aqueous formaldehyde solution can be used as a formaldehyde source.

The urea solution A withdrawn from the urea solution is controlled to be 0.5 or more in terms of the molar ratio of urea/formaldehyde, and therefore polymerization scarcely takes place during heating and concentrating.

The urea solution A is reacted with formaldehyde at a condition of a pH of 6.5 or higher, and therefore a concentration operation is possible while preventing the polymerization of urea with formaldehyde.

Further, the urea exposed to heating can be controlled to a very small amount as compared with the total amount of urea, and therefore the formation of biuret which is a by-product contained in the product can be neglected.

EXAMPLES

The examples of the present invention shall specifically be described below with reference to the examples.

Example 1

In a plant for producing urea at 41,667 kg/h, urea solution A at 417 kg/h was withdrawn from the urea solution sent to the granulating facility 5 (spouted, fluidized bed granulating facility disclosed in JP-B-4-63729) and sent to the mixer 1 through the line 12. Further, aqueous formaldehyde solution (formalin) of 694 kg/h containing 30% by weight of formaldehyde was sent to the mixer 1 through the line 13 so that the ratio of urea to formalin was 1. Ammonia at 10 kg/h was sent through the line 14 so that the pH of the mixer 1 was about 8, and urea was reacted with formaldehyde. Heat generated in the mixer 1 was removed by cooling water to maintain the temperature of the mixed solution at 70 to 75° C.

The mixed solution was sent to the evaporator 2 and concentrated to 75% at an operating pressure of an absolute pressure of 150 mm Hg at 80° C. The concentration was carried out by heating by steam, and the amount of steam was about 310 kg/h. Water separated from the mixed solution in the form of steam was 264 kg/h, and it was cooled, condensed and recovered in the vacuum condenser 3. The concentrated urea/formaldehyde mixed solution thus obtained was sent to the granulating facility 5 through the line 16 after being mixed with the remaining urea solution B. The urea solution thus obtained containing about 0.5% by weight of formaldehyde was used to prepare granular urea in the granulating facility 5.

The granular urea thus obtained was dried further in the granulating facility 5, and granular urea finally containing a water content of 0.2% by weight was obtained. This product was characterized by having a high mechanical strength and less damage during transportation. For example, a product crushing strength of 25 to 35 N/2.7 mm was obtained.

Comparative Example 1

Mixer 1 was operated in the same manner as in Example 1, except that the ammonia mixed with the urea solution A was changed from 10 kg/hr to 2 kg/hr. Initially, the pH was 8 but it lowered to 6 at the outlet of the mixer, and a polymer was formed, which made any following operation impossible.

Example 2

The same procedure as that in Example 1 was repeated, except that the operating condition of the evaporator 2 was changed to an absolute pressure of 120 mm Hg to concentrate the mixed solution to 80%.

The urea solution for granular urea thus obtained was used to prepare prill urea by a conventional method, and prill urea having a water content of 0.3% by weight was obtained. This product had a product crushing strength of 10 to 15 N/1.7 mm.

We claim:

1. A process for preparing granulates of urea from a solution or melt of urea, which comprises the steps of:
   providing a urea solution which is obtained directly from a urea production facility;
   dividing the urea solution into a first portion A and a second portion B;
   mixing the first portion A with ammonia and an aqueous formaldehyde solution to form a mixture A, the amount of formaldehyde being from 0.3 to 0.6% by weight based on the amount of urea fed to a means for granulating;
   feeding the mixture A to a means for concentrating the mixture A;
   concentrating the mixture A to form a concentrated mixture A;
   mixing the concentrated mixture A with a second portion B to form a resultant mixture;
   feeding the resultant mixture to the means for granulating; and
   granulating the resultant mixture.

2. The process as claimed in claim 1, in which the first portion A is mixed with the ammonia and the aqueous formaldehyde solution at a mole ratio of urea to formaldehyde of at least 0.5.

3. The process as claimed in claim 1, in which the mixing of the first portion A with the ammonia and the aqueous formaldehyde solution and the concentrating step are conducted at a pH value of at least 6.5.

4. The process as claimed in claim 1, in which the content of formaldehyde in the aqueous formaldehyde solution is from 30 to 37% by weight.

5. The process as claimed in claim 1, wherein the means for granulating is a prilling tower.

6. The process as claimed in claim 1, wherein the means for granulating is a fluidized, spouted bed granulator.

7. The process as claimed in claim 1, wherein the first portion A is mixed with the ammonia and the aqueous formaldehyde solution at a temperature of from 40 to 100° C.

8. A process for preparing granulates of urea from a solution or melt of urea, which comprises the steps of:
   providing a urea solution which is obtained directly from a urea production facility;
   dividing the urea solution into a first portion A and a second portion B;
   mixing the first portion A with ammonia and an aqueous formaldehyde solution to form a mixture A, the mole ratio of urea to formaldehyde being at least 0.5 and the amount of formaldehyde being from 0.3 to 0.6% by weight based on the amount of urea fed to a means for granulating;

maintaining mixture A at a temperature of from 40 to 100° C. and a pH of at least 6.5 during the mixing of the first portion A with the aqueous formaldehyde solution;

feeding the mixture A to a means for concentrating the mixture A;

concentrating the mixture A to form a concentrated mixture A;

mixing the concentrated mixture A with the second portion B to form a resultant mixture;

feeding the resultant mixture to a means for granulating; and granulating the resultant mixture.

9. The process as claimed in claim 8, wherein the means for granulating is a prilling tower.

10. The process as claimed in claim 8, wherein the means for granulating is a fluidized, spouted bed granulator.

11. The process as claimed in claim 8, wherein the content of formaldehyde in the aqueous formaldehyde solution is from 30 to 37% by weight.

* * * * *